US010932759B2

(12) United States Patent
Yamamoto

(10) Patent No.: US 10,932,759 B2
(45) Date of Patent: *Mar. 2, 2021

(54) ULTRASOUND DIAGNOSTIC APPARATUS AND DATA PROCESSING METHOD

(71) Applicant: FUJIFILM CORPORATION, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1099 days.

This patent is subject to a terminal disclaimer.

(21) Appl. No.: 14/531,386

(22) Filed: Nov. 3, 2014

(65) Prior Publication Data

US 2015/0045667 A1    Feb. 12, 2015

Related U.S. Application Data

(63) Continuation of application No. PCT/JP2013/064378, filed on May 23, 2013.

(30) Foreign Application Priority Data

May 25, 2012   (JP) .............................. JP2012-120012

(51) Int. Cl.
*A61B 8/00* (2006.01)
*A61B 8/08* (2006.01)
*A61B 8/14* (2006.01)

(52) U.S. Cl.
CPC .............. *A61B 8/58* (2013.01); *A61B 8/4483* (2013.01); *A61B 8/5207* (2013.01); *A61B 8/585* (2013.01);
(Continued)

(58) Field of Classification Search
None
See application file for complete search history.

(56) References Cited

U.S. PATENT DOCUMENTS 6,132,375 A * 10/2000 Napolitano ......... G01S 7/52046
600/443
2005/0283076 A1* 12/2005 Hangiandreou ..... A61B 8/0825
600/443
(Continued)

FOREIGN PATENT DOCUMENTS

| JP | 2-209135 A | 8/1990 |
| JP | 11-104130 A | 4/1999 |
| JP | 2009-142680 A | 7/2009 |

OTHER PUBLICATIONS

Japanese Office Action, dated Oct. 13, 2015, for corresponding Japanese Application No. 2012-120012, with a partial English translation.
(Continued)

*Primary Examiner* — Katherine L Fernandez
(74) *Attorney, Agent, or Firm* — Birch, Stewart, Kolasch & Birch, LLP

(57) ABSTRACT

In the ultrasound diagnostic apparatus, the ultrasonic wave transmitter/receiver transmits and receives an ultrasonic beam to a subject to generate reception data using ultrasonic wave transmission/reception elements arranged in one direction; the delay correction unit corrects a delay time of the reception data to align a phase of the reception data; the reception aperture range determination unit determines a reception aperture range of reception data, which is used when producing an ultrasound image from reception data after correction of the delay time, based on a signal value of the reception data after correction of the delay time in an arrangement direction of the ultrasonic wave transmission/reception elements; and the image producer produces an
(Continued)

ultrasound image by performing phase matching addition of the reception data after correction of the delay time corresponding the reception aperture range and performing data processing.

18 Claims, 9 Drawing Sheets

(52) U.S. Cl.
CPC ............... *A61B 8/14* (2013.01); *A61B 8/461* (2013.01); *A61B 8/5269* (2013.01)

(56) References Cited

U.S. PATENT DOCUMENTS

| | | | | |
|---|---|---|---|---|
| 2011/0044133 | A1* | 2/2011 | Tokita | G01S 7/52047 367/87 |
| 2011/0306886 | A1* | 12/2011 | Daft | A61B 8/0825 600/459 |
| 2012/0095343 | A1* | 4/2012 | Smith | A61B 8/4483 600/447 |
| 2013/0253325 | A1* | 9/2013 | Call | G01S 15/8913 600/447 |
| 2014/0058266 | A1* | 2/2014 | Call | A61B 8/14 600/448 |
| 2015/0049578 | A1* | 2/2015 | Hoctor | G01S 7/52046 367/7 |
| 2017/0281136 | A1* | 10/2017 | Mochizuki | A61B 8/5253 |

OTHER PUBLICATIONS

International Preliminary Report on Patentability issued in PCT/JP2013/064378 dated Dec. 4, 2014 (Forms PCT/IB/338, PCT/IB/373 and PCT/ISA/237).

International Search Report issued in PCT/JP2013/064378, dated Jul. 2, 2013.

* cited by examiner

ULTRASOUND DIAGNOSTIC APPARATUS AND DATA PROCESSING METHOD

CROSS-REFERENCE TO RELATED APPLICATIONS

This application is a Continuation of PCT International Application No. PCT/JP2013/064378 filed on May 23, 2013, which claims priority under 35 U.S.C. § 119(a) to Japanese Application No. 2012-120012 filed on May 25, 2012. The above application is hereby expressly incorporated by reference, in its entirety, into the present application.

BACKGROUND OF THE INVENTION

The present invention relates to an ultrasound diagnostic apparatus and a data processing method for creating and displaying an ultrasound image of a diagnostic region of a subject using an ultrasonic wave.

An ultrasound diagnostic apparatus using an ultrasound image has hitherto been put into practical use in the field of medicine. In general, the ultrasound diagnostic apparatus has an ultrasound probe in which a transducer array is installed, and an apparatus body connected to the ultrasound probe. In the ultrasound diagnostic apparatus, an ultrasonic beam is transmitted from the ultrasound probe toward a subject, an ultrasonic echo, which is a reflected ultrasonic beam from the subject, is received by the ultrasound probe to acquire a reception signal, and the acquired reception signal is electrically processed by the apparatus body to produce an ultrasound image.

In the conventional ultrasound diagnostic apparatus, the value of the sound speed of ultrasonic wave set for the entire apparatus is fixed to a certain value assuming that the sound speed of ultrasonic wave in the living body of the subject is constant.

However, since the sound speed changes depending on differences in tissues such as a fat layer and a muscular layer in the living body, the sound speed of ultrasonic wave in the subject (hereinafter, referred to as an ambient sound speed) is not uniform. In addition, since the thickness of the fat layer or the muscular layer is different between a fat subject and a thin subject, there are individual differences in the ambient sound speed for each subject.

As described above, in the conventional ultrasound diagnostic apparatus, the sound speed of ultrasonic wave set for the entire apparatus (hereinafter, referred to as a set sound speed) is fixed to a certain value. In this case, the more the ambient sound speed, which is the sound speed in the subject, deviates from the set sound speed, the more the arrival time of the reflected wave (ultrasonic echo) deviates from the delay time set for the ultrasonic wave transmission/reception circuit. For this reason, there has been a problem in that the focusing is degraded, and accordingly, the quality of the obtained ultrasound image is degraded.

In contrast, as shown in FIG. 10, the first embodiment described in JP 2009-142680 A discloses an ultrasound diagnostic apparatus which includes an ultrasonic wave transmitter/receiver 2 that drives a probe 1 to transmit ultrasonic waves to a subject and processes signals of the reflected echo from the subject, a phasing adder 3 that aligns the phases of the reception signals processed by the ultrasonic wave transmitter/receiver 2, and an image display unit 4 that displays the signals from the phasing adder 3 as an image, and in the ultrasound diagnostic apparatus, a plurality of values of switching interval of the optimal reception wave delay correction value are stored in advance in a focus switching interval storage unit 7 for each observation region or each physique of the subject, a focus switching interval instruction unit 8 sets an arbitrary switching interval of reception wave delay correction value in the focus switching interval storage unit 7, and the phasing adder 3 adjusts the focus according to the set switching interval of reception wave delay correction value.

SUMMARY OF THE INVENTION

However, even if a plurality of values of the switching interval of reception wave delay correction value are prepared and appropriately switched as in the focus adjusting method disclosed in JP 2009-142680 A, there has been a problem in that adjustment to the optimal focusing is difficult if the quality of the original reception signal is poor.

The present invention has been made to solve the above-described problems, and it is an object of the present invention to provide an ultrasound diagnostic apparatus and a data processing method capable of adjusting an ultrasound image so as to have the optimal focus even if the quality of the original reception signal of the ultrasound image is poor.

To attain the above object, the present invention provides an ultrasound diagnostic apparatus, comprising:

an ultrasonic wave transmitter/receiver configured to transmit ultrasonic beam to a subject and receive an ultrasonic echo, which is a reflected ultrasonic beam from the subject, to generate reception data using a plurality of ultrasonic wave transmission/reception elements arranged in one direction;

a delay correction unit configured to correct a delay time, which is a difference in arrival time of the ultrasonic echo in the reception data, to align a phase of the reception data;

a reception aperture range determination unit configured to determine a reception aperture range of reception data, which is used when producing an ultrasound image from reception data after correction of the delay time, based on a signal value of the reception data after correction of the delay time in an arrangement direction of the ultrasonic wave transmission/reception elements; and an image producer configured to produce an ultrasound image by performing phase matching addition of the reception data after correction of the delay me corresponding to the reception aperture range and performing predetermined data processing.

Also, the present invention provides a data processing method, comprising steps of:

generating reception data by transmitting an ultrasonic beam to a subject and receiving an ultrasonic echo, which is a reflected ultrasonic beam from the subject, using a plurality of ultrasonic wave transmission/reception elements arranged in one direction;

correcting a delay time, which is a difference in arrival time of the ultrasonic echo in the reception data, to align a phase of the reception data;

determining a reception aperture range of reception data, which is used when producing an ultrasound image from reception data after correction of the delay time, based on a signal value of the reception data after correction of the delay time in an arrangement direction of the ultrasonic wave transmission/reception elements; and producing an ultrasound image by performing phase matching addition of the reception data after correction of the delay time corresponding to the reception aperture range and performing predetermined data processing.

In the present invention, the reception aperture range of the reception data which is used when producing an ultrasound image is determined based on the signal value of the reception data after correction of delay time in the arrangement direction of the ultrasonic wave transmission/reception elements, and the ultrasound image is produced using the reception data corresponding to the determined reception aperture range.

Thus, according to the present invention, it is possible to obtain the reception data having a good signal/noise (S/N) ratio by excluding the reception data having a poor S/N ratio at both ends in the arrangement direction of the ultrasonic wave transmission/reception elements. As a result, even if the quality of the original reception data or image signal is poor, it is possible to adjust the ultrasound image so as to have the optimal focus.

DETAILED DESCRIPTION OF THE INVENTION

Hereinafter, an ultrasound diagnostic apparatus and a data processing method of the present invention will be described in detail based on preferred embodiments shown in the accompanying drawings.

Figure 1:
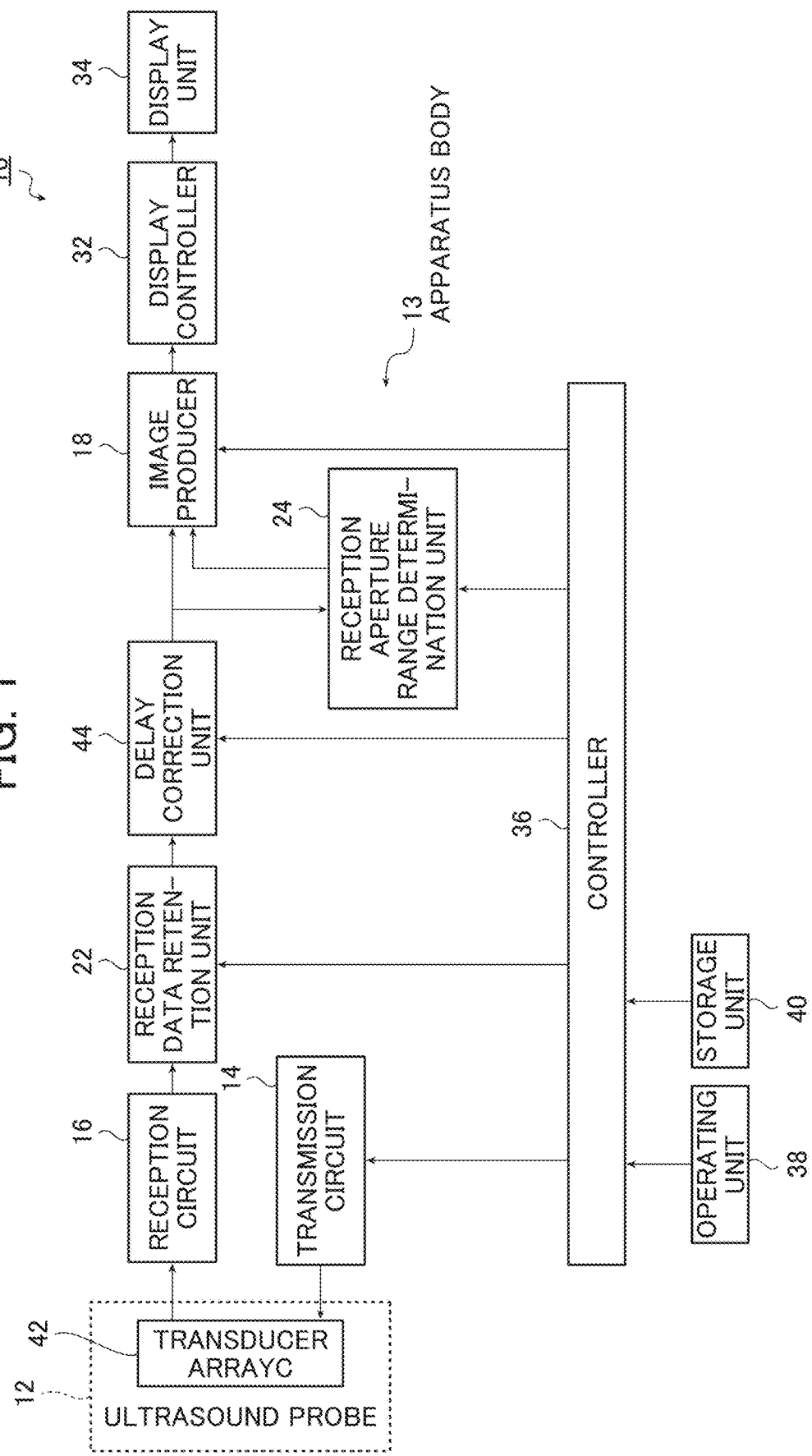
FIG. 1 is a block diagram showing the configuration of a first embodiment of an ultrasound diagnostic apparatus for carrying out a data processing method of the present invention.

FIG. 1 is a block diagram showing the configuration of a first embodiment of an ultrasound diagnostic apparatus for carrying out a data processing method of the present invention.

An ultrasound diagnostic apparatus 10 shown in FIG. 1 is configured with an ultrasound probe 12 and an apparatus body 13 connected to the ultrasound probe 12.

The apparatus body 13 includes a transmission circuit 14, a reception circuit 16, a reception data retention unit 22, a delay correction unit 44, a reception aperture range determination unit 24, an image producer 18, a display controller 32, a display unit 34, a controller 36, an operating unit 38, and a storage unit 40.

The ultrasound diagnostic apparatus 10 is an apparatus which transmits an ultrasonic beam from the ultrasound probe 12 toward a subject, receives an ultrasonic echo which is a reflected ultrasonic beam from the subject, and produces and displays an ultrasound image from the reception signal of the ultrasonic echo.

The ultrasound probe 12 is used in a state of being brought into contact with a subject, and has a transducer array 42 which is used in a usual ultrasound diagnostic apparatus.

The transducer array 42 has a plurality of ultrasound transducers (ultrasonic wave transmission/reception elements) which are one-dimensionally or two-dimensionally arranged. When an ultrasound image is captured, each of the plurality of ultrasound transducers transmits an ultrasonic beam toward the subject in accordance with a driving signal supplied from the transmission circuit 14, receives an ultrasonic echo from the subject (that is, the ultrasonic beam reflected by the subject), and outputs a reception signal.

Each ultrasound transducer is constituted by a vibrator in which electrodes are formed at both ends of a piezoelectric substance formed of, for example, a piezoelectric ceramic represented by PZT (lead zirconate titanate), a polymer piezoelectric element represented by PVDF (polyvinylidene fluoride), a piezoelectric single crystal represented by PMN-PT (lead magnesium niobate-lead titanate solid solution), or the like.

If a pulsed or continuous-wave voltage is applied across the electrodes of the vibrator, the piezoelectric substance expands and contracts, whereby pulsed or continuous-wave ultrasonic waves are generated from the vibrator, and the generated ultrasonic waves are synthesized to form an ultrasonic beam. When receiving propagating ultrasonic wave, each vibrator expands and contracts to generate an electric signal and the electric signal is output as the reception signal of the ultrasonic wave.

Meanwhile, in the apparatus body 13, the transmission circuit 14 includes a plurality of pulsers, for example. The transmission circuit 14 performs transmission focusing to adjust the amount of delay of each driving signal (timing of applying a driving signal) so that ultrasonic waves transmitted from the plurality of ultrasound transducers of the transducer array 42 form an ultrasonic beam based on the transmission delay pattern selected by the controller 36, and supplies the adjusted driving signals to the plurality of ultrasound transducers. Thus, the ultrasonic beams are transmitted from the plurality of ultrasound transducers to the subject.

The reception circuit 16 amplifies the reception signal supplied from each ultrasound transducer of the transducer array 42, and A/D (analog/digital) converts the amplified reception signal to generate reception data.

The ultrasound probe 12, the transmission circuit 14, and the reception circuit 16 constitute an ultrasonic wave transmitter/receiver in the present invention.

Here, the transmission delay pattern is pattern data of the delay time that is given to a driving signal in order to form an ultrasonic beam in a desired direction with ultrasonic waves transmitted from the plurality of ultrasound transducers. The reception delay pattern is pattern data of the delay time that is given to a reception signal in order to extract an ultrasonic echo from a desired direction with ultrasonic waves received by the plurality of ultrasound transducers.

A plurality of transmission delay patterns and a plurality of reception delay patterns are stored in the storage unit 40 in advance. The controller 36 selects one transmission delay pattern and one reception delay pattern from the plurality of transmission delay patterns and the plurality of reception delay patterns stored in the storage unit 40 and outputs control signals to the transmission circuit 14 and the delay correction unit 44 according to the selected transmission delay pattern and reception delay pattern, thereby performing transmission/reception control of the ultrasonic wave.

Then, the reception data retention unit (a reception data memory) 22 stores the reception data generated by the reception circuit 16 in a sequential manner. In addition, the reception data retention unit 22 stores information regarding the frame rate (for example, parameters indicating the depth of the reflection position of the ultrasonic wave, the density of scanning lines, and the width of a field of vision), which is input from the controller 36, so as to be associated with the reception data described above.

The reception data retained in the reception data retention unit 22 is sequentially read, and is supplied to the delay correction unit 44.

In the present embodiment, it is not essential to provide the reception data retention unit 22. When the reception data retention unit 22 is not provided, the reception data generated by the reception circuit 16 is supplied to the delay correction unit 44.

Since the distances between the respective ultrasound transducers and the ultrasonic reflection source in the subject are different, the time taken for the ultrasonic echo to reach each ultrasound transducer is different.

The delay correction unit 44 aligns the phase of the reception data by correcting the difference in arrival time (delay time) of the ultrasonic echo in the reception data of a luminance image supplied from the reception data retention unit 22 based on the reception delay pattern selected by the controller 36.

In the present embodiment, the delay correction unit 44 aligns the phase by delaying the reception data by the difference in arrival time (delay time) of the ultrasonic echo.

A reception aperture range determination unit 24 determines a reception aperture range (the number of channels) of the reception data, which is used when an image producer 18 produces an ultrasound image from the reception data after delay time correction, based on the signal value of the reception data after delay time correction in the arrangement direction of the plurality of ultrasound transducers arranged in one direction.

In the present embodiment, the reception aperture range determination unit 24 determines the range of the reception data after delay time correction, in which the signal value in the arrangement direction of the ultrasound transducers is equal to or greater than a predetermined threshold value, as a reception aperture range.

A reception aperture range setting signal that is a determination result of the reception aperture range is output from the reception aperture range determination unit 24.

Here, the reception aperture range is the range of reception data in the arrangement direction of the ultrasound transducers that is used when producing an ultrasound image. That is, assuming that the number of ultrasound transducers in the arrangement direction is N, the total number of channels of reception data is N.

Assuming that the reception aperture range is n (n is an integer of N or less), in the present embodiment, an ultrasound image is produced by using the reception data of the respective ranges of n/2 from the reception data of the channel at the center in the arrangement direction of the ultrasound transducers toward the reception data of channels at both ends.

In addition, the predetermined threshold value is preferably set based on the S/N ratio of the distribution of the reception data after delay time correction in the arrangement direction of the ultrasound transducers. As the predetermined threshold value, for example, a fixed value may be set in the reception aperture range determination unit 24 in advance, or an arbitrary value may be set in the reception aperture range determination unit 24 under the control of the controller 36 according to an instruction input by an operator using the operating unit 38, which will be described later.

Then, the image producer 18 produces an ultrasound image based on the reception data after delay time correction supplied from the delay correction unit 44 and the reception aperture range setting signal supplied from the reception aperture range determination unit 24. That is, the image producer 18 produces an ultrasound image using the reception data after delay time correction of the channels corresponding to the reception aperture range designated by the reception aperture range setting signal.

Figure 2:
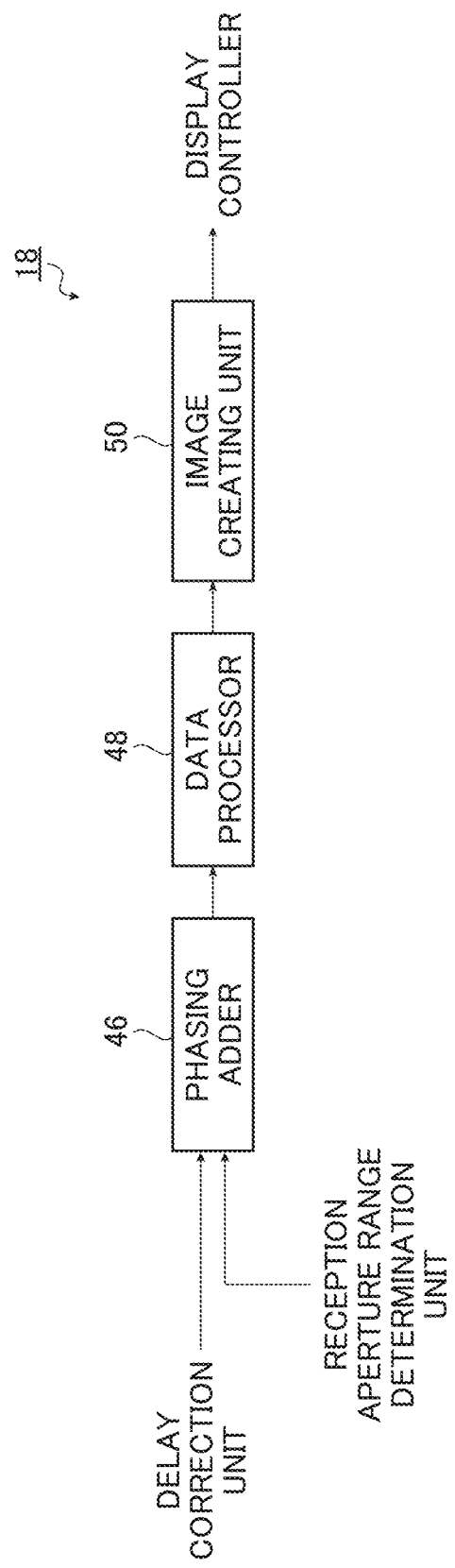
FIG. 2 is a block diagram showing the configuration of an image producer shown in FIG. 1.

As shown in FIG. 2, the image producer 18 includes a phasing adder 46, a data processor 48, and an image creating unit 50.

The phasing adder 46 performs reception focus processing digitally by performing phase matching addition on the reception data after delay time correction supplied from the delay correction unit 44.

When there is another ultrasonic reflection source at a position different from the position of the ultrasonic reflection source, the arrival time of the reception signal from the other ultrasonic reflection source is different. Therefore, the phase of the reception signal from the other ultrasonic reflection source is cancelled by addition in the phasing adder 46. Thus, the reception signal from the ultrasonic reflection source becomes greatest, thereby becoming in focus. By the reception focus processing, the focus of the ultrasonic echo is narrowed down and reception data (sound ray signal) is generated.

The data processor 48 performs predetermined data processing on the reception data having been subjected to reception focus processing by the phasing adder 46.

In the present embodiment, the data processor 48 generates a B-mode image signal (image signal of a luminance image in which the amplitude of the ultrasonic echo is expressed by the brightness (luminance) of a point), which is tomographic image information regarding tissue within the subject, by performing correction of attenuation due to the distance depending on the depth of the reflection position of the ultrasonic wave and then performing envelope detection processing.

The generated B-mode image signal is an image signal obtained by a scanning system different from a usual television signal scanning system. Therefore, the data processor 48 converts (raster-converts) the generated B-mode image signal into a usual image signal, for example, an image signal according to the television signal scanning system (for example, an NTSC system).

The image creating unit 50 performs various necessary image processing, such as gradation processing, on the B-mode image signal which has been subjected to the data processing by the data processor 48, and then, creates an ultrasound image corresponding to the B-mode image signal after the image processing.

Subsequently, the display controller 32 causes the display unit 34 to display the ultrasound image produced by the image producer 18.

The display unit 34 is, for example, a display device such as an LCD, and displays the ultrasound diagnostic image (a video and a still image) and various setting screens under the control of the display controller 32.

The controller 36 controls the respective constituents of the ultrasound diagnostic apparatus 10 on the basis of instructions input from the operating unit 38 by an operator.

The operating unit 38 is an input device for receiving instructions input by the operator, and may be constituted by a keyboard, a mouse, a trackball, a touch panel, or the like.

The storage unit 40 stores an operation program for causing the controller 36 to execute control of the respective constituents of the ultrasound diagnostic apparatus 10, the transmission delay pattern and reception delay pattern, or the like, and may be constituted by a recording medium such as a hard disk, a flexible disk, an MO, an MT, a RAM, a CD-ROM a DVD-ROM, or the like.

The delay correction unit 44, the reception aperture range determination unit 24, the image producer 18, and the display controller 32 are constituted by a CPU (a computer) and an operation program for causing the CPU to execute various processing, but these may be constituted by digital circuits.

Figure 3:
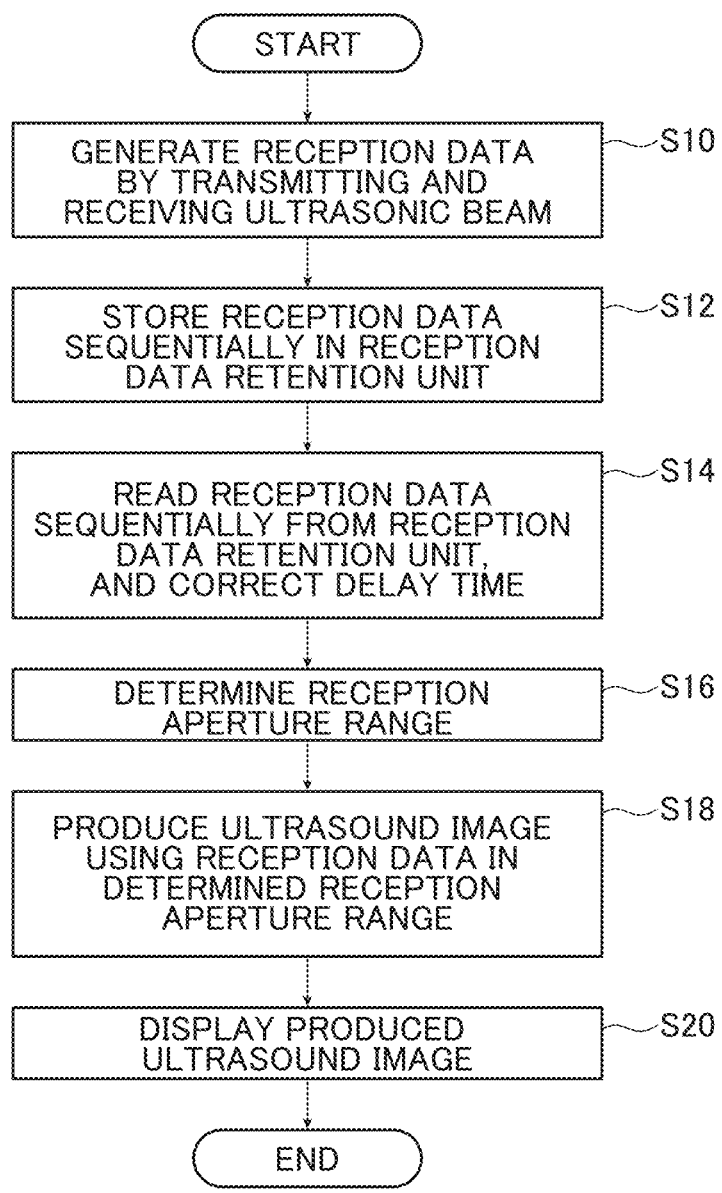
FIG. 3 is a flowchart showing the flow of the process in the ultrasound diagnostic apparatus shown in FIG. 1.
Figure 4:
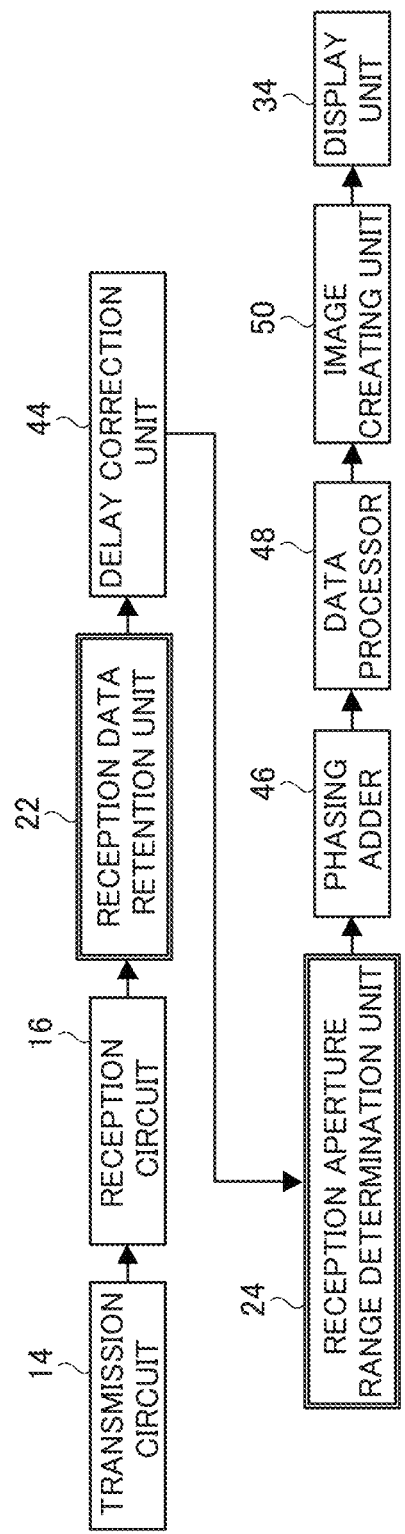
FIG. 4 is a conceptual diagram showing the flow of the process in the ultrasound diagnostic apparatus shown in FIG. 1.

Next, the operation of the ultrasound diagnostic apparatus 10 will be described with reference to the flowchart shown in FIG. 3 and the conceptual diagram shown in FIG. 4. FIG. 3 is a flowchart showing the flow of the process in the ultrasound diagnostic apparatus shown in FIG. 1, and FIG. 4 is a conceptual diagram showing the flow of the process.

An ultrasound probe 12 is brought into contact with a subject, and an instruction of an operator is input from the operating unit 38 to start ultrasound diagnosis.

When the ultrasound diagnosis is started, the controller 36 sets a transmission direction of the ultrasonic beam and a reception direction of the ultrasonic echo for each ultrasound transducer, and selects a transmission delay pattern according to the transmission direction of the ultrasonic beam and selects a reception delay pattern according to the reception direction of the ultrasonic echo. Then, the controller 36 outputs control signals to the transmission circuit 14 and the delay correction unit 44 according the selected transmission delay pattern and the selected reception delay pattern, thereby performing transmission/reception control of the ultrasonic wave.

In response to this, in the transmission circuit 14, a transmission focus of the driving signal of each ultrasound transducer is performed based on the selected transmission delay pattern, and the ultrasonic beams are transmitted from the plurality of ultrasound transducers to a subject.

Then, the ultrasonic echo from the subject is received by the plurality of ultrasound transducers, and the reception signals are output from the plurality of ultrasound transducers.

The reception circuit 16 generates reception data by amplifying the reception signal supplied from each ultrasound transducer and performing A/D conversion of the amplified signal (step S10).

The reception data generated by the reception circuit 16 is sequentially stored in the reception data retention unit 22 (step S12).

Then, the reception data stored in the reception data retention unit 22 is sequentially read, and is supplied to the delay correction unit 44.

The delay correction unit 44 aligns the phase by correcting the delay time of the reception data supplied from the reception data retention unit 22 based on the selected reception delay pattern (step S14).

Meanwhile, the reception aperture range determination unit 24 determines the reception aperture range of the reception data based on the signal value of the reception data after delay time correction in the arrangement direction of the ultrasound transducers, and outputs a reception aperture range setting signal that is the determination result (step S16).

In the present embodiment, the reception aperture range determination unit 24 determines the range of the reception data after lay time correction, in which the signal value (amplitude) in the arrangement direction of the ultrasound transducers is equal to or greater than a predetermined threshold value, as a reception aperture range.

The image producer 18 produces an ultrasound image using the reception data after delay time correction of the channels corresponding to the reception aperture range designated by the reception aperture range setting signal (step S18).

That is, the phasing adder 46 digitally performs reception focus processing on the reception data after delay time correction, thereby generating reception data in which the focus of the ultrasonic echo is narrowed down.

Then, the data processor 48 generates a B-mode image signal by performing data processing on the reception data which has been subjected to the reception focus processing, and the image creating section 50 creates an ultrasound image from the B-mode image signal. Thus, an ultrasound image corresponding to the reception data of the reception aperture range designated by the reception aperture range setting signal is created.

Finally, the ultrasound image produced by the image producer 18 is displayed on the display unit 34 under the control of the display controller 32 (step S20).

Figure 5A:
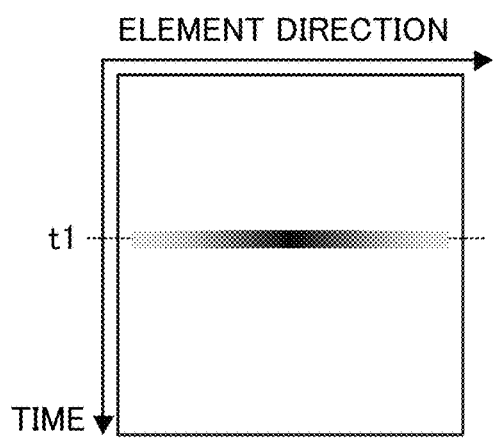
FIG. 5A is a conceptual diagram showing reception data after delay time correction.
Figure 5B:
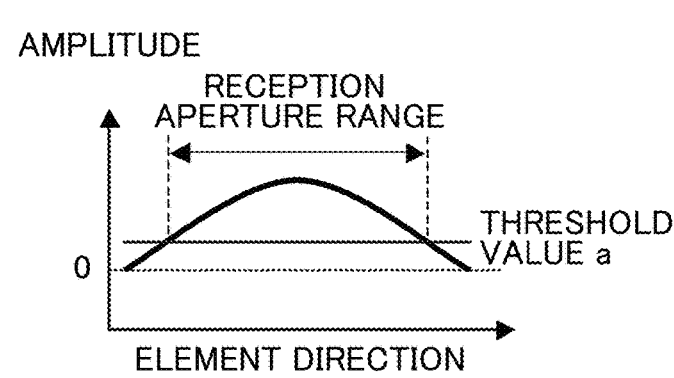
FIG. 5B is a graph showing the amplitude of the reception data at time t1.

Here, FIG. 5A is a conceptual diagram showing the reception data after delay time correction, and FIG. 5B is a graph showing the amplitude of the reception data at time t1. In FIG. 5A, the horizontal axis indicates an arrangement direction (element direction) of ultrasound transducers (ultrasonic wave transmission/reception elements), and the vertical axis indicates time. In FIG. 5B, the horizontal axis indicates an arrangement direction (element direction) of ultrasound transducers, and the vertical axis indicates a signal value (amplitude) of reception data.

As shown in FIGS. 5A and 5B, in general, reception data at the center in the arrangement direction of ultrasound transducers has larger signal strength (larger amplitude) than that of reception data at both ends in the arrangement direction, and the S/N ratio of the reception data at the center in the arrangement direction is good.

Therefore, when the phasing adder 46 performs phase matching addition of the reception data after delay time correction supplied from the delay correction unit 44, the reception aperture range is made narrow if the S/N ratio of the reception data at both ends is poor. Thus, c is possible to obtain reception data having a good S/N ratio by performing phase matching addition in a state where the reception data at both ends is excluded. However, if the reception aperture range is made narrow, the weight of each piece of reception data before phase matching addition becomes large. Accordingly, for example, if a certain piece of reception data has a noise, reception data after phase matching addition is greatly influenced by the noise.

As described above, the reception aperture range for adjusting the ultrasound image so as to have the optimal focus differs depending on the quality of the original reception data or reception signal.

For example, in the case of point reflection in which the ultrasonic reflection source is isolated, a possibility that the reception data will have little noise is high. Therefore, in this case, it is thought that narrowing the reception aperture range is preferable. In contrast, in the case where point reflections are densely present as the ultrasonic reflection source such as a calcified portion of breast cancer, a possibility that the reception data will have noise is high. Therefore, in this case, it is thought that increasing the reception aperture range is preferable.

In the ultrasound diagnostic apparatus 10 of the present embodiment, as shown in FIG. 5B, the range of the reception data after delay time correction in which the amplitude (signal value) in the arrangement direction of the ultrasound transducers is equal to or greater than a predetermined threshold value a is determined as the reception aperture range, and the ultrasound image is produced using the reception data of the channels corresponding to the determined reception aperture range. In addition, the reception aperture range can be appropriately changed by changing the value of the predetermined threshold value a.

Therefore, since it is possible to obtain reception data having a good S/N ratio by excluding the reception data at both ends having a poor S/N ratio, it is possible to adjust the ultrasound image so as to have the optimal focus, even if the quality of the original reception data or image signal is poor.

Next, a second embodiment of the ultrasound diagnostic apparatus of the present invention will be described.

Figure 6:
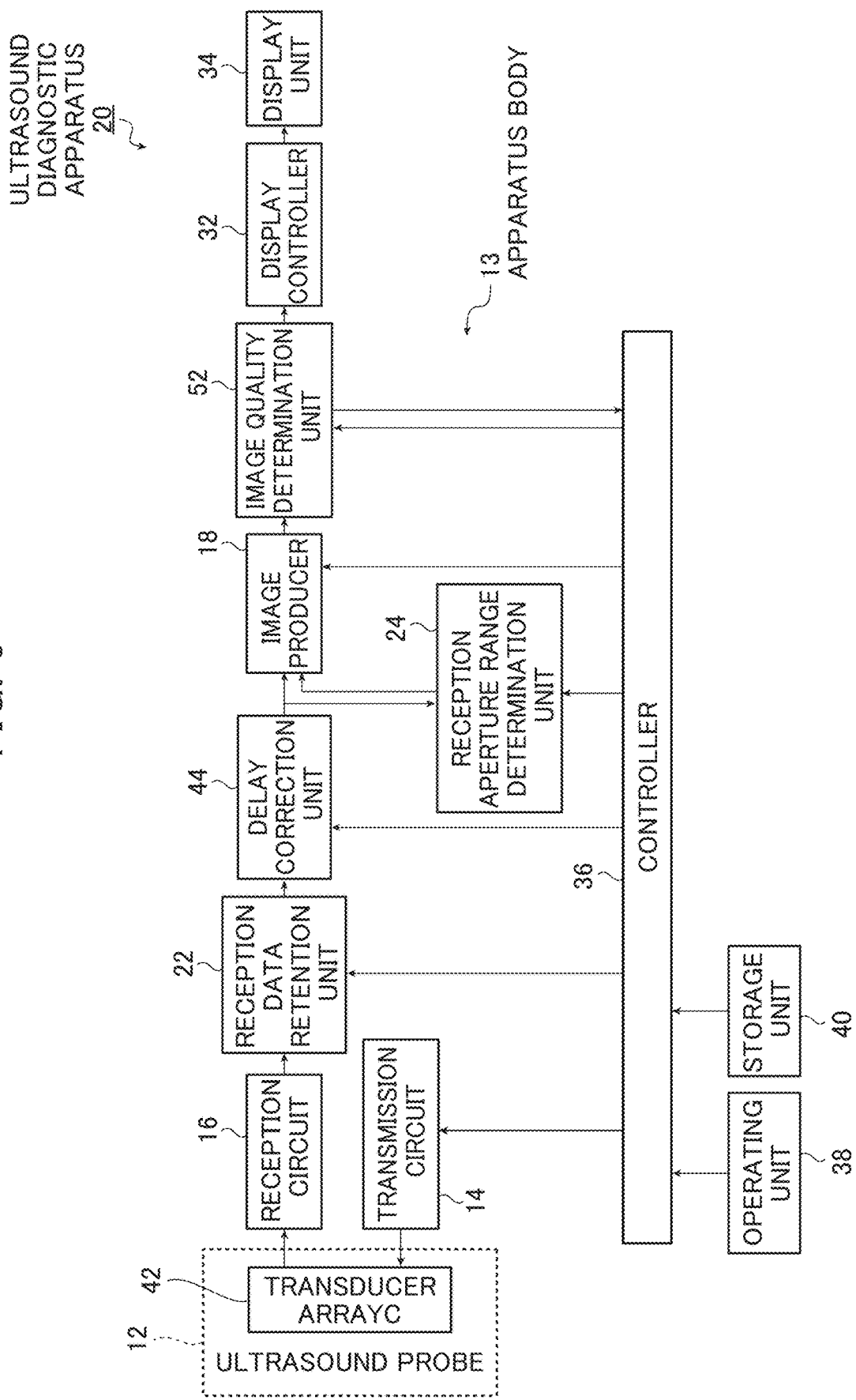
FIG. 6 is a block diagram showing the configuration of a second embodiment of an ultrasound diagnostic apparatus for carrying out a data processing method of the present invention.

FIG. 6 is a block diagram showing the configuration of the second embodiment of the ultrasound diagnostic apparatus for carrying out a data processing method of the present invention.

As shown in FIG. 6, an ultrasound diagnostic apparatus 20 of the present embodiment is configured to further include an image quality determination unit 52 in the ultrasound diagnostic apparatus 10 of the first embodiment shown in FIG. 1. Accordingly, the same components are denoted by the same reference numerals, and explanation thereof will be omitted.

The image quality determination unit 52 determines the image quality of an ultrasound image produced by the image producer 18.

The image quality determination unit 52 determines the image quality of the ultrasound image based on the luminance value, sharpness, or the like of the ultrasound image produced by the image producer 18, for example. That is, the image quality determination unit 52 determines the image quality according to whether or not the luminance value, sharpness, or the like of the ultrasound image produced by the image producer 18 has a value equal to or greater than a threshold value with respect to the luminance value, sharpness, or the like corresponding to an ultrasound image having a predetermined image quality.

Figure 7:
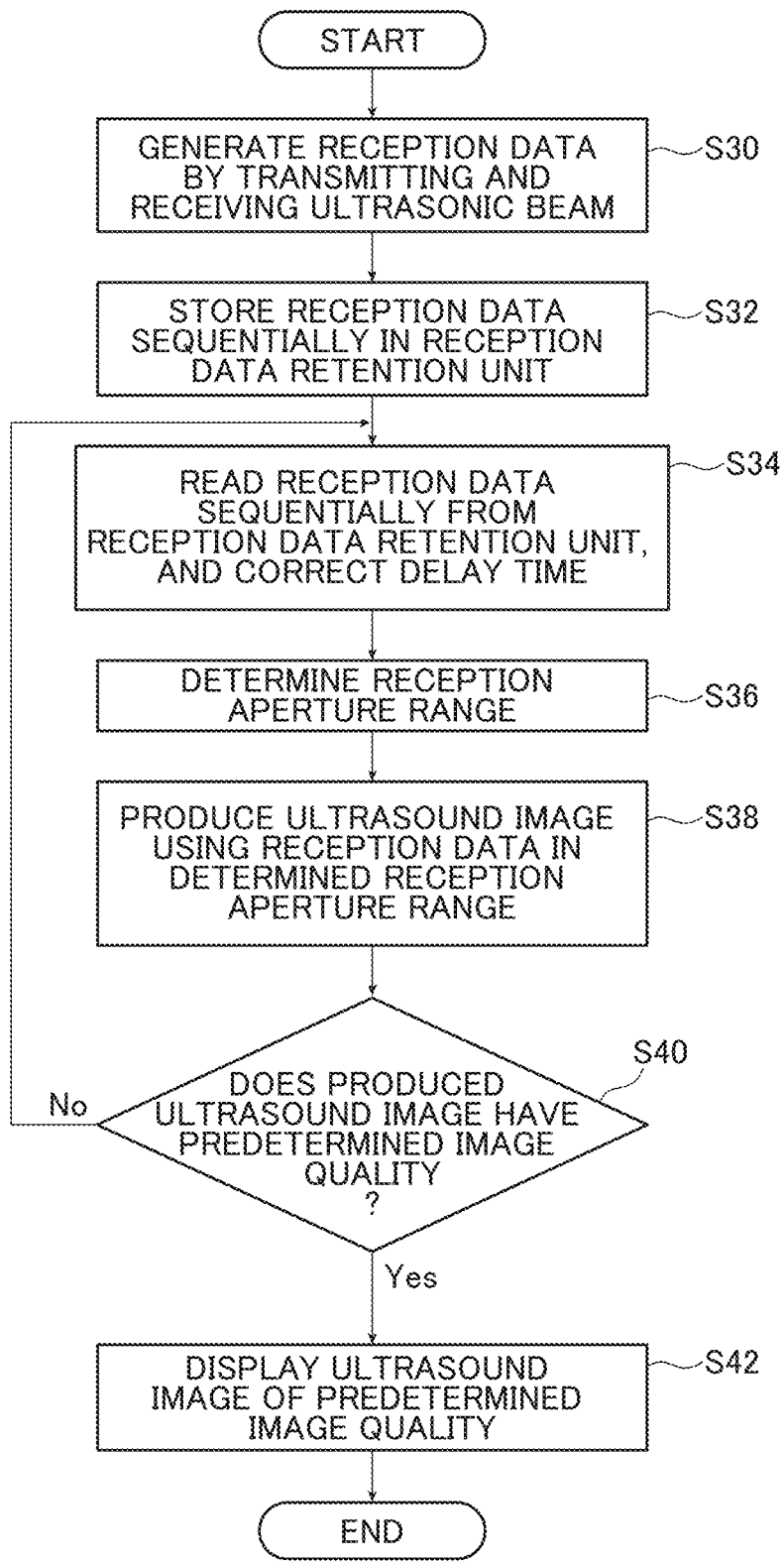
FIG. 7 is a flowchart showing the flow of the process in the ultrasound diagnostic apparatus shown in FIG. 6.
Figure 8:
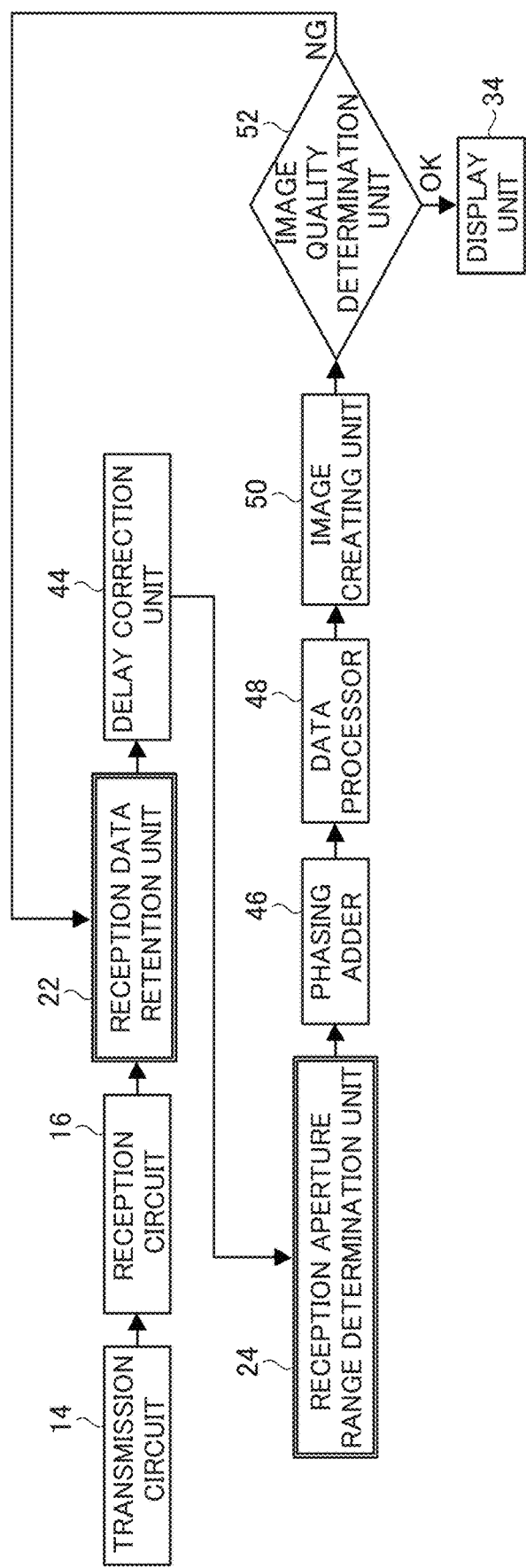
FIG. 8 is a conceptual diagram showing the flow of the process in the ultrasound diagnostic apparatus shown in FIG. 6.

Next, the operation of the ultrasound diagnostic apparatus 20 will be described with reference to the flowchart shown in FIG. 7 and the conceptual diagram shown FIG. 8. FIG. 7 is a flowchart showing the flow of the process in the ultrasound diagnostic apparatus shown in FIG. 6, and FIG. 8 is a conceptual diagram showing the flow of the process.

Here, steps S30, S32, S34, S36, and S38 shown in the flowchart of FIG. 7 are the same as steps S10, S12, S14, S16, and S18 shown in the flowchart of FIG. 3, respectively.

That is, in the ultrasound diagnostic apparatus 20 of the present embodiment, when ultrasound diagnosis is started, an ultrasonic wave transmitter/receiver transmits and receives ultrasonic beams to and from the subject to generate reception data (step S30), and the reception data is sequentially stored in the reception data retention unit 22 (step S32).

Then, the reception data is read from the reception data retention unit 22, and the delay correction unit 44 corrects the delay time of the reception data based on the reception delay pattern selected by the controller 36 (step S34).

Meanwhile, the reception aperture range determination unit 24 determines the reception aperture range of the reception data based on the reception data after delay time correction, and outputs a reception aperture range setting signal that is the determination result (step S36).

Then, the image producer 18 produces an ultrasound image using the reception data after delay time correction of the channels corresponding to the reception aperture range designated by the reception aperture range setting signal (step S38).

Subsequently, when the image quality determination unit 52 determines that the ultrasound image produced by the image producer 18 does not have a predetermined image quality ("No" in step S40), the controller 36 returns to step S34 and performs control such that the setting of the value of the sound speed (set sound speed) of the ultrasonic wave is changed to re-correct the delay time of the reception data (step S34), the reception aperture range is determined (step S36), and an ultrasound image is produced using the reception data of the determined reception aperture range (step S38).

Here, the correction of the delay time of the reception data when the setting of the set sound speed is changed will be described.

Figure 9:
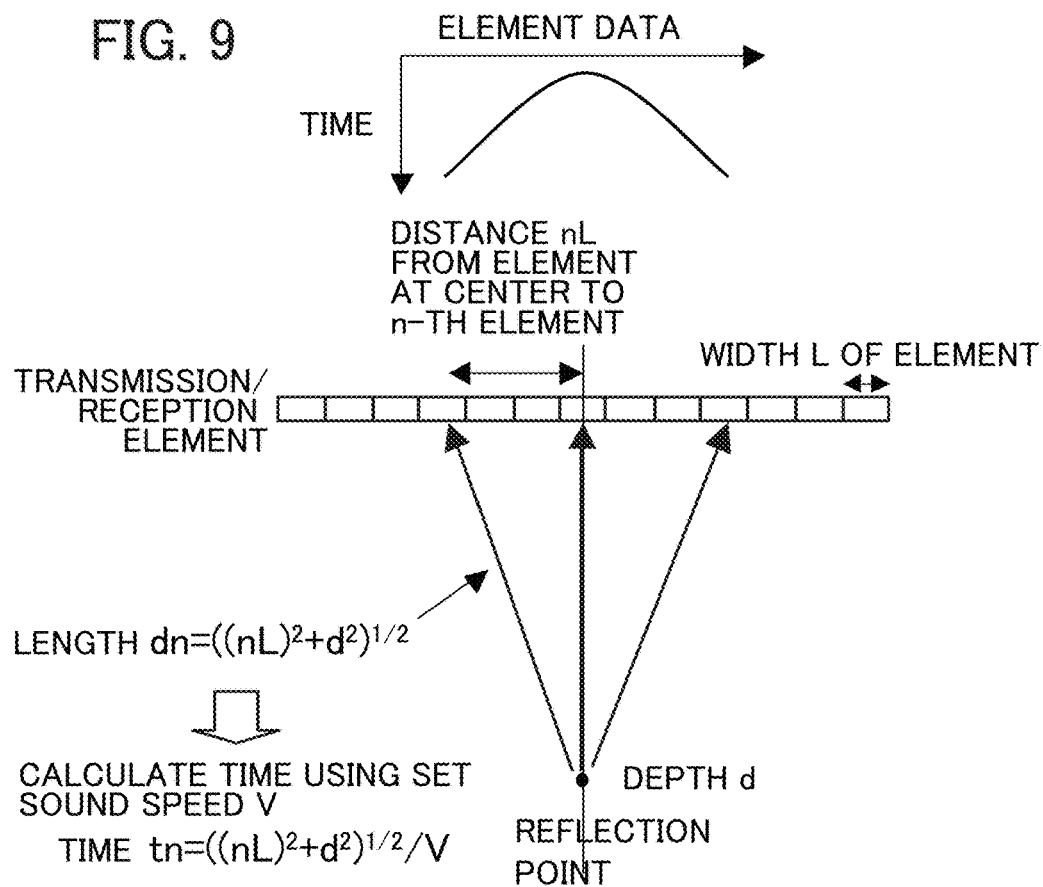
FIG. 9 is a conceptual diagram showing a state in which the delay time of reception data is corrected based on the set sound speed.
Figure 10:
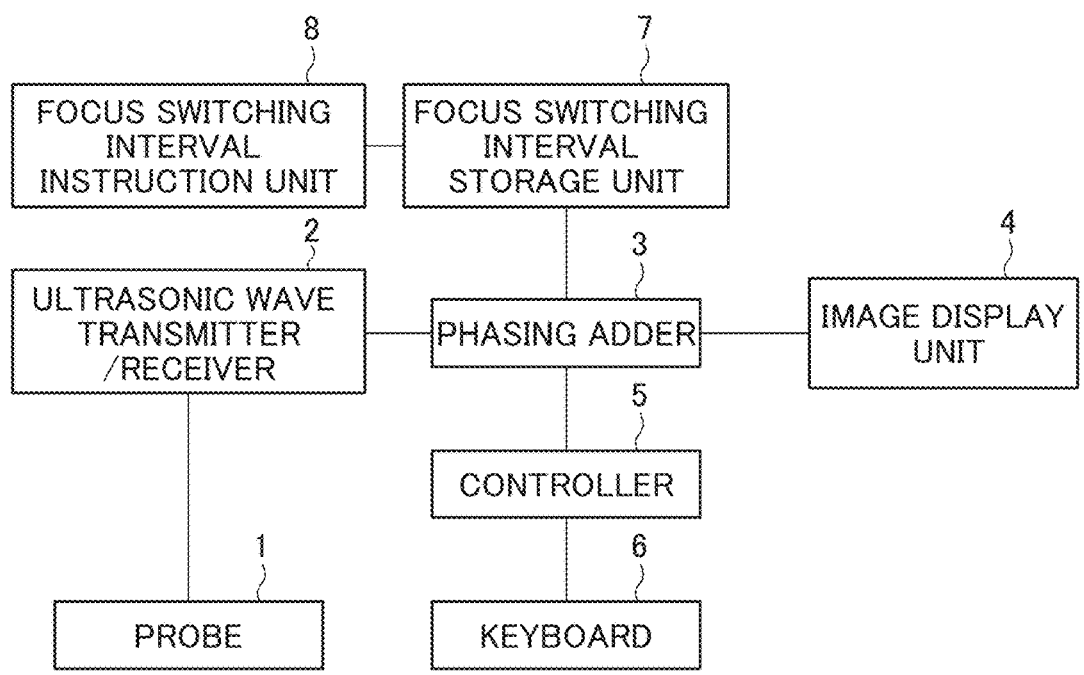
FIG. 10 is a block diagram showing the configuration of an ultrasound diagnostic apparatus disclosed in JP 2009-142680 A.

FIG. 9 is a conceptual diagram showing a state in which the delay time of reception data is corrected based on the set sound speed. As shown in FIG. 9, a case is considered in which a plurality of ultrasound transducers (ultrasonic wave transmission/reception elements) of the ultrasound probe 12 are arranged in a row in a horizontal direction in FIG. 9.

Here, assuming that the width of each ultrasound transducer in the arrangement direction of ultrasound transducers is L, the distance from the ultrasound transducer at the center in the arrangement direction to the n-th ultrasound transducer toward the end of the arrangement is nL.

As shown in FIG. 9, assuming that the reflection point of the ultrasonic wave is present at a position at a distance (depth) d from the ultrasound transducer at the center in a direction perpendicular to the arrangement direction, a distance (length) $d_n$ between the n-th ultrasound transducer and the reflection point is calculated by Expression (1).

$$d_n = ((nL)^2 + d^2)^{1/2} \tag{1}$$

Therefore, time $t_n$ until the ultrasonic wave from the reflection point is received by the n-th ultrasound transducer is calculated by Expression (2) using a set sound speed V.

$$t_n = d_n/V = ((nL)^2 + d^2)^{1/2}/V \tag{2}$$

Since the distances between the respective ultrasound transducers and the reflection point are different as described above, in this example, as shown in the graph in the upper part of FIG. 9, the time $t_n$ becomes longer toward the ultrasound transducer at the end of the arrangement.

That is, assuming that the time until the ultrasonic wave from the reflection point is received by the ultrasound transducer at the center is $t_1$, the ultrasonic wave received by the n-th ultrasound transducer is delayed by time $\Delta t=t_n-t_1$ with respect to the ultrasonic wave received by the ultrasound transducer at the center. The delay correction unit 44 corrects the delay time expressed by the time $\Delta t$ for the reception data corresponding to each ultrasound transducer. This delay time $\Delta t$ is referred to as a reception delay pattern. As described above, the delay time $\Delta t$ of each piece of reception data is calculated from the set sound speed and the distance calculated from the geometric arrangement of the reflection point and each ultrasound transducer.

Although the example described above is a case where the ultrasound probe 12 is a linear probe, the same thinking can be applied to a convex prove except for the difference in the shape of the probe.

The above-described operation is repeated until the image quality determination unit 52 determines that the ultrasound image produced by the image producer 18 has a predetermined image quality in step S40 ("Yes" in step S40).

When the image quality determination unit 52 determines that the ultrasound image produced by the image producer 18 has a predetermined image quality ("Yes" in step S40), the ultrasound image of the predetermined image quality produced by the image producer 18 is displayed on the display unit 34 under the control of the display controller 32 (step S42).

In the ultrasound diagnostic apparatus 20 of the present embodiment, when the ultrasound image produced by the image producer 18 does not have a predetermined image quality, changing the setting of the sound speed value of the ultrasonic wave to re-correct the delay time of the reception data and producing the ultrasound image by use of the reception data of the reception aperture range is repeated until the image quality determination unit 52 determines that the ultrasound image produced by the image producer 18 has the predetermined image quality. In addition, whenever the setting of the sound speed value of the ultrasonic wave is changed, the reception aperture range can be appropriately changed by changing the value of the predetermined threshold value a.

Therefore, it is possible to optimize the delay time correction of the reception data and to obtain the reception data having a good S/N ratio by excluding the reception data having a poor S/N ratio at both ends, and consequently, it is possible to adjust the ultrasound image so as to have the optimal focus even if the quality of the original reception data or image signal is poor.

In addition, in the respective embodiments described above, the reception data is generated using all ultrasound transducers, and the ultrasound image is produced using the reception data after delay time correction corresponding to the reception aperture range determined by the reception aperture range determination unit 24. However, the present invention is not limited thereto, and reception data may be generated using only ultrasound transducers corresponding to the determined reception aperture range.

The present invention is basically as described above.

Hereinbefore, the present invention has been described in detail, but needless to say, the present invention is not limited to the above-described embodiments, and may be improved or modified in various ways within a scope that does not depart from the gist of the present invention.

What is claimed is:

1. An ultrasound diagnostic apparatus, comprising:
    an ultrasonic wave transmitter and receiver that transmits an ultrasonic beam to a subject and receives an ultrasonic echo, which is a reflected ultrasonic beam from the subject, to generate reception data using a plurality of ultrasonic wave transmission and reception elements arranged in one direction; and
    a processor configured to:
    correct a delay time of the reception data to generate corrected reception data, the delay time being a difference in arrival time of the ultrasonic echo in the reception data;
    determine a reception aperture range of the corrected reception data by selecting a portion of the corrected reception data corresponding to the reception aperture range from the corrected reception data, the reception aperture range being a range of the corrected reception data in the one direction of the plurality of ultrasonic wave transmission and reception elements, wherein the processor is further configured to determine the reception aperture range as corresponding to the portion of the corrected reception data in which a signal amplitude or luminance value is equal to or greater than a predetermined threshold value; and
    produce an ultrasound image by performing phase matching addition of the portion of the corrected reception data and thereafter performing predetermined data processing.

2. The ultrasound diagnostic apparatus according to claim 1,
    wherein the predetermined threshold value is set based on an S/N ratio of distribution of the corrected reception data in the one direction of the plurality of ultrasonic wave transmission and reception elements.

3. The ultrasound diagnostic apparatus according to claim 1,
    wherein the ultrasonic wave transmitter and receiver generates the reception data using only ultrasonic wave transmission and reception elements corresponding to the reception aperture range.

4. The ultrasound diagnostic apparatus according to claim 1, wherein the processor is further configured to retain the reception data generated by the ultrasonic wave transmitter and receiver, and
    wherein the processor is further configured to correct a delay time of the reception data that is supplied.

5. The ultrasound diagnostic apparatus according to claim 4, wherein the processor is further configured to determine an image quality of the ultrasound image that is produced.

6. The ultrasound diagnostic apparatus according to claim 5,
    wherein the processor is further configured to determine the image quality of the ultrasound image based on a luminance value of the ultrasound image that is produced.

7. The ultrasound diagnostic apparatus according to claim 6,
    wherein the processor is further configured to determine the image quality of the ultrasound image that is produced according to whether or not the ultrasound image that is produced has a value equal to or greater than a threshold value corresponding to an ultrasound image having a predetermined image quality.

8. The ultrasound diagnostic apparatus according to claim 5,
    wherein the processor is further configured to determine the image quality of the ultrasound image based on sharpness of the ultrasound image that is produced.

9. The ultrasound diagnostic apparatus according to claim 5, further comprising a controller configured to perform control such that, when the processor determines that the ultrasound image that is produced does not have a predetermined image quality, producing an ultrasound image by changing a setting of a value of a sound speed of an ultrasonic wave and re-correcting the delay time of the reception data is repeated until the processor determines that the ultrasound image that is produced has the predetermined image quality.

10. A data processing method, comprising steps of:
generating reception data by transmitting an ultrasonic beam to a subject and receiving an ultrasonic echo, which is a reflected ultrasonic beam from the subject, using a plurality of ultrasonic wave transmission and reception elements arranged in one direction;
correcting a delay time of the reception data to generate corrected reception data, the delay time being a difference in arrival time of the ultrasonic echo in the reception data;
determining a reception aperture range of the corrected reception data by selecting a portion of the corrected reception data corresponding to the reception aperture range from the corrected reception data, the reception aperture range being a range of the corrected reception data in the one direction of the plurality of ultrasonic wave transmission and reception elements, wherein the reception aperture range is determined as corresponding to the portion of the corrected reception data in which a signal amplitude or luminance value is equal to or greater than a predetermined threshold value; and
producing an ultrasound image by performing phase matching addition of the portion of the corrected reception data and thereafter performing predetermined data processing.

11. The data processing method according to claim 10, wherein the predetermined threshold value is set based on an S/N ratio of distribution of the corrected reception data in the one direction of the plurality of ultrasonic wave transmission and reception elements.

12. The data processing method according to claim 10, wherein the reception data is generated using only ultrasonic wave transmission and reception elements corresponding to the reception aperture range.

13. The data processing method according to claim 11, further comprising a step of retaining the generated reception data in a reception data retention memory,
wherein the delay time of the reception data read from the reception data retention memory is corrected.

14. The data processing method according to claim 13, further comprising a step of determining image quality of the produced ultrasound image.

15. The data processing method according to claim 14, wherein the image quality of the ultrasound image is determined based on a luminance value of the produced ultrasound image.

16. The data processing method according to claim 15, wherein the image quality of the produced ultrasound image is determined according to whether or not the produced ultrasound image has a value equal to or greater than a threshold value corresponding to an ultrasound image having a predetermined image quality.

17. The data processing method according to claim 14, wherein the image quality of the ultrasound image is determined based on sharpness of the produced ultrasound image.

18. The data processing method according to claim 14, further comprising a step of performing control such that, when it is determined that the produced ultrasound image does not have a predetermined image quality, producing an ultrasound image by changing a setting of a value of a sound speed of an ultrasonic wave and re-correcting the delay time of the reception data is repeated until the produced ultrasound image has the predetermined image quality.

* * * * *